United States Patent [19]
Palanker

[11] Patent Number: 6,135,998
[45] Date of Patent: Oct. 24, 2000

[54] METHOD AND APPARATUS FOR PULSED PLASMA-MEDIATED ELECTROSURGERY IN LIQUID MEDIA

[75] Inventor: Daniel V. Palanker, Sunnyvale, Calif.

[73] Assignee: Board of Trustees of the Leland Stanford Junior University, Palo Alto, Calif.

[21] Appl. No.: 09/270,401

[22] Filed: Mar. 16, 1999

[51] Int. Cl.$^7$ ................................. A61B 18/12
[52] U.S. Cl. ................. 606/39; 606/34; 606/45
[58] Field of Search ............... 606/34, 37–41, 606/45–50

[56] References Cited

U.S. PATENT DOCUMENTS

| | | | |
|---|---|---|---|
| 3,903,891 | 9/1975 | Brayshaw | 606/45 |
| 4,429,694 | 2/1984 | McGreevy | 128/303.14 |
| 5,300,068 | 4/1994 | Rosar et al. | 606/34 |
| 5,509,916 | 4/1996 | Taylor | 606/13 |
| 5,669,907 | 9/1997 | Platt, Jr. et al. | 606/48 |
| 5,720,745 | 2/1998 | Farin et al. | 606/49 |
| 5,871,469 | 2/1999 | Eggers et al. | 604/114 |

FOREIGN PATENT DOCUMENTS 2225534  6/1990  United Kingdom ...................... 606/39

OTHER PUBLICATIONS

Palanker, D, *Electrical alternative to pulsed fiber–delivered lasers in microsurgery*, J. Appl. Phys. 81(11), pp. 7673–7680, 1997.

*Primary Examiner*—Lee Cohen
*Attorney, Agent, or Firm*—Luman Intellectual Property Services

[57] ABSTRACT

A method for performing electrosurgery using submicrosecond, high-power electrical pulses applied to an electrosurgical probe endface. The probe endface has an area of about 200–1000 microns$^2$. The pulses have a duration less than 300 nanoseconds, and preferably have very fast rise-times and very fast falltimes (e.g. less than 100 nanoseconds). The pulses also have power dissipation greater than 500 Watts (e.g. 800–2500 Watts), or voltage greater than 1.5 kV (e.g. 2–3 kV). These pulse characteristics provide for reduced collateral damage, and effective cutting of tissue. Cutting is mainly provided by plasma streamers which are formed on the probe tip endface. However, cutting is also provided by shock waves formed by the discharges. The method is applicable to microsurgical procedures such as retinal surgery and capsulotomy. Also disclosed are electrical circuits for performing the method.

47 Claims, 6 Drawing Sheets

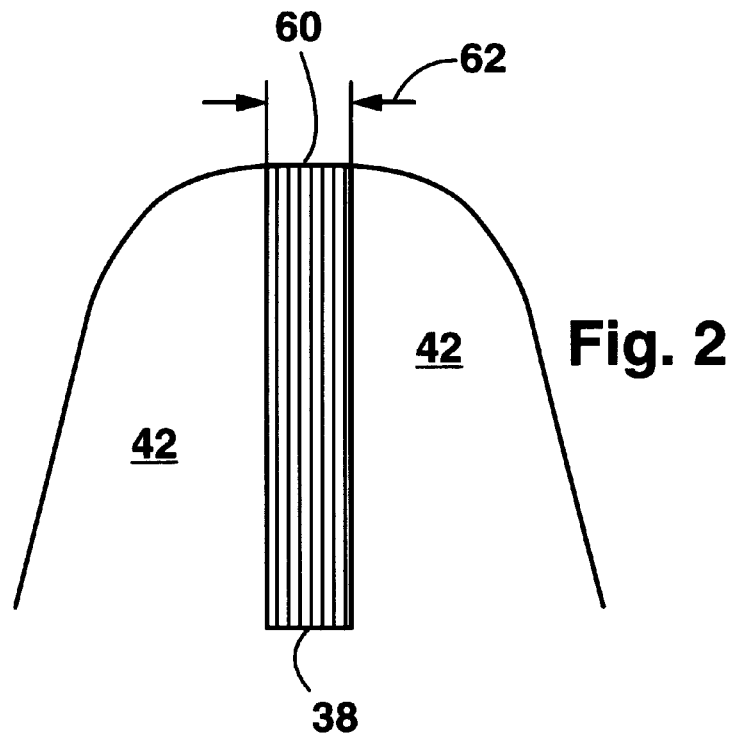
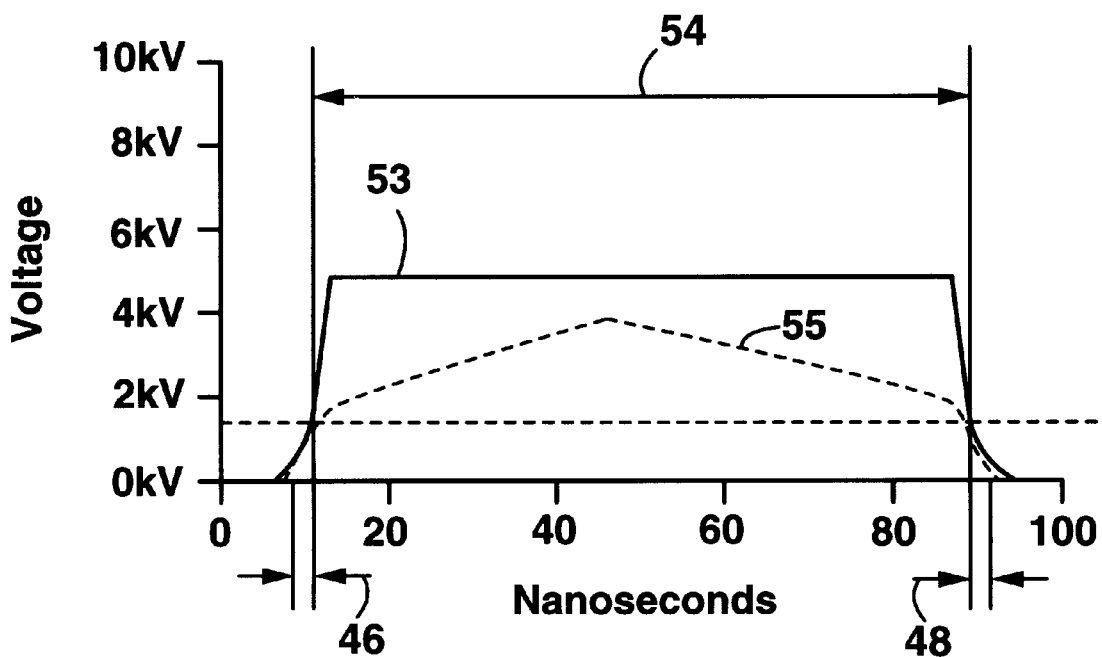

METHOD AND APPARATUS FOR PULSED PLASMA-MEDIATED ELECTROSURGERY IN LIQUID MEDIA

FIELD OF THE INVENTION

This invention relates generally to electrosurgery. More particularly, it relates to a method for electrosurgery using short duration, high voltage pulses in liquid.

BACKGROUND OF THE INVENTION

Electrosurgery is a technique used in the medical arts for cutting, ablation and coagulation of tissues. In electrosurgery, electrical energy is applied to the tissue or to conductive media in proximity to the tissue. The electrical energy can heat, evaporate and ionize the tissue.

Most commonly in electrosurgery, the electrical energy is applied as a continuous wave (CW) or pulses of radiofrequency energy. The RF energy is applied with a probe having a pair (or more) of electrodes. Tissue in proximity to the electrodes is heated and destroyed or ablated. Electrosurgery with RF energy is usually used in medical procedures where direct heating is desired for tissue modification, destruction, or removal. Examples of such procedures include coagulation of blood vessels, tissue dissection in general surgery (electric knife), and skin and cartilage removal.

A shortcoming of using RF energy in electrosurgery is that, for some applications, the RF energy heats too broad a region, resulting in undesired collateral damage to surrounding tissues. Use of RF energy is particularly undesirable for delicate microsurgical procedures where RF energy tends to result in unacceptably large areas of collateral damage.

Certain pulsed electrosurgical devices have been proposed for specific applications. R. Vorreuther et al. *Journal of Urology*, 153:849–853 (1995) use high energy pulses (tens of milliJoules) with a relatively long duration (hundreds of microseconds) to generate shock waves which destroy the targeted tissue (e.g. kidney stones). The method of Vorreuther obviously cannot be applied to delicate microsurgical procedures. Also, the long pulse durations taught by Vorreuther tend to result in excessive collateral damage. Another disadvantage of the teachings of Vorreuther is that the device has a short lifetime of less than 100 pulses due to the high energy of the pulses.

U.S. Pat. No. 4,429,694 discloses an electrosurgical technique where AC voltage pulses are used to coagulate tissues by heat generation. The AC pulses generate plasma in air which is applied to the tissues to be coagulated. U.S. Pat. No. 5,300,068 teaches the use of relatively long duration pulses (about 200 microseconds) for electrosurgery. U.S. Pat. No. 5,509,916 discloses the combination of laser pulses and electrical pulses. The laser pulse provides more precise localization of the electrical discharges. The prior art does not teach methods for precise electrosurgical cutting of tissues applicable to microsurgery in liquid where a very small (tens of microns or less) collateral damage zone is important.

"Electrical Alternative to Pulsed Fiber Delivered Lasers in Microsurgery", *Journal of Applied Physics* 81(11): 7673–7680 (1997) by Daniel Palanker et al. discloses a method for intraocular microsurgery based on cavitation bubble generation by electrical discharge. In this approach, the expanding cavitation bubble is used to provide cutting action. A limitation of using the cavitation bubble for cutting is that only very soft tissues (e.g. retinal tissues) can be cut. Relatively hard tissues such as eye lenses, lens capsules (e.g. in a capsulotomy procedure) or irises cannot be cut by the method disclosed by Palanker. Yet another disadvantage of the method of Palanker is that cavitation bubbles produce substantial collateral damage to surrounding tissues due to generation of water flow during bubble collapse.

Pulsed lasers have commonly been used in delicate surgical procedures where collateral damage must be avoided (i.e. vitreoretinal surgery). However, a great disadvantage of laser-based devices is that they are relatively expensive, costing upwards of $100,000. Electrosurgical systems are typically much less expensive.

OBJECTS AND ADVANTAGES OF THE INVENTION

Accordingly, it is a primary object of the present invention to provide an improved method for electrosurgery that:
1) produces very little collateral damage to tissues surrounding targeted tissues;
2) is capable of cutting relatively hard tissues such as lenses, lens capsules, and irises;
3) is less expensive than laser based surgical devices;
4) can be used in microsurgical procedures;
5) is capable of precise dissection of biological tissue in liquid media.

These and other objects and advantages will be apparent upon reading the following description and accompanying drawings.

SUMMARY OF THE INVENTION

These objects and advantages are attained by a method for using an electrosurgical probe immersed in liquid media or tissue. The electrosurgical probe has a first electrode and a second electrode. The first electrode has an endface area A in close proximity to tissue to be cut. The method has the step of applying to the first electrode an electrical pulse such that plasma streamers are formed from the endface. The plasma streamers develop in the liquid medium or tissue. The electrical pulse has a voltage of at least 1.5 kV for a nonzero duration of less than 300 nanoseconds. The electrical pulse has a 100 volt to 1.5 kV V-risetime of less than 100 nanoseconds, and a 1.5 kV to 100 volt V-falltime of less than 300 nanoseconds. The endface area is less than 10000 microns$^2$.

The present invention also includes the method of applying to the first electrode an electrical pulse wherein the pulse dissipates at least 500 Watts for a nonzero duration less than 300 nanoseconds. The pulse has a P-risetime from 50 Watts to 500 Watts of less than 100 nanoseconds. Also, the pulse has a P-falltime from 500 Watts to 50 Watts of less than 150 nanoseconds. The endface area A is less than 10000 microns$^2$.

The present method can also be characterized in terms of a peak power dissipation of the pulse. In this characterization, the pulse has a power dissipation greater than 500 watts for a duration less than 300 nanoseconds. The pulse has a risetime from 10% of peak power to 90% of peak power which is less than 100 nanoseconds. The pulse also has a falltime from 90% of peak power to 10% of peak power less than 200 nanoseconds. The peak power dissipation can be greater than 800 Watts, 1000 Watts, or 1500 Watts, for example.

The present invention also includes an apparatus for electrosurgically cutting tissue according to the present invention. The apparatus has a high voltage source for providing a voltage of at least 2 kV, a probe, a discharge switch, and a shunt switch. The probe has a first electrode and a second electrode. The discharge switch is connected between the high voltage source and first electrode such that, when closed, the discharge switch applies high voltage to the first electrode. The shunt switch is connected between the first and second electrodes.

Alternatively, the shunt switch is replaced with only a shunt resistor. In this case, the shunt resistor has a resistance lower than a normal state (i.e. no plasma present) resistance between the first and second electrodes. Preferably, the shunt resistor has a resistance in the range of 1–5 kOhm.

DESCRIPTION OF THE FIGURES

FIG. 2 shows a closeup view of a probe tip of the present invention.

FIG. 3 shows a characterization of electrical pulses according to the method of the present invention.

DETAILED DESCRIPTION

The present invention provides methods for cutting tissues in liquid media using short duration electrical discharges. The electrical discharges used have sufficient power dissipated from a sufficiently small electrode surface so that plasma streamers are produced which extend from the electrode surface. The plasma streamers are produced in the tissue or liquid medium surrounding the tissue. The plasma streamers ionize and evaporate tissue (or liquid), thereby producing high pressure shock and acoustic waves. The high temperature of the plasma streamers and the shock waves produced provide effective cutting of tissue. The electrode surface is preferably in contact with the tissue being cut, but can also be spaced apart from the tissue being cut. The present invention uses DC electrical pulses.

Figure 1:
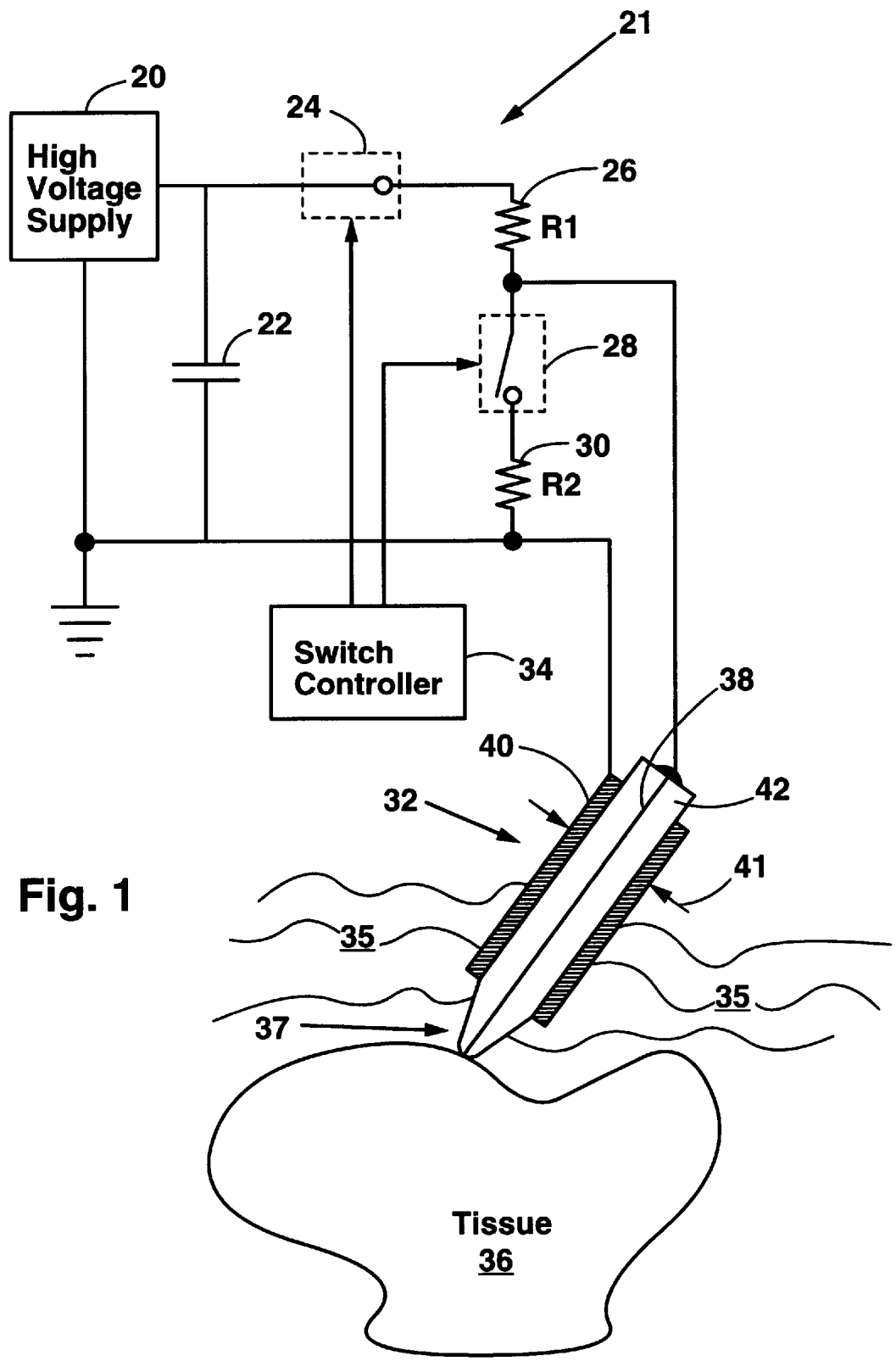
FIG. 1 shows a preferred embodiment of the present invention in use cutting tissue.

FIG. 1 shows a preferred electrical circuit 21 for performing the method of the present invention. The apparatus has a high voltage supply 20. The supply 20 provides 2–10 kilovolts, for example. The voltage supply 20 is connected to a capacitor 22 (e.g. at least 10–50 picofarads) and a high speed, high voltage discharge switch 24. The discharge switch is connected to a discharge resistor (R1) 26, a shunt switch 28, a shunt resistor (R2) 30, and an electrosurgical probe 32. The discharge switch 24 and shunt switch 28 are controlled by switch controller 34. The electrosurgical probe 32 is shown in contact with tissue 36 to be electrosurgically cut. The tissue 36 to be cut is surrounded by conductive liquid media 35 such as tissue fluid, intraocular fluid, or other physiological liquids. The liquid 35 may be present in a thin layer (e.g. less than 0.1 mm thick) covering the tissue 36.

Probe 34 has two electrodes: an inner electrode 38 and a coaxial outer electrode 40. The inner electrode and outer electrode are separated by a dielectric material 42 such as glass or fused silica. The outer electrode 40 has a much larger surface area compared to inner electrode 38. The liquid media 35 is in contact with the outer electrode 40. Outer electrode is always connected to ground. The probe has a tip 37 where the inner electrode 38 is not covered by dielectric material 42. The probe has a diameter 41 of about 1.0 mm, tapering to 0.2 mm near the tip 37. Alternatively, the probe 32 may have a non-coaxial geometry such as two electrodes with comparable exposed surface areas embedded in insulating material. Many electrosurgical probes are known in the art.

In performing the method of the present invention, the outer electrode 40 can also be in contact with the tissue 36. This would be the case, for example, if the probe were fully inserted into the tissue 36. Physical contact with media 35 or tissue 36 provides electrical contact with media 35 or tissue 36.

FIG. 2 shows a closeup view of the probe tip 37. The inner electrode 38 and dielectric material 42 are shown. The inner electrode has an endface 60. The endface is preferably about 10–30 microns across 62. The endface may have an exposed surface area of about 600 microns$^2$, for example. The inner electrode 38 can be a cylindrical wire, for example, in which case endface 60 is circular. In use, the inner electrode is eroded by ablation. A larger endface provides a longer probe lifetime because more inner electrode material must be eroded before probe is no longer useful. A larger endface also generally requires more powerful electrical pulses. A smaller endface has a shorter lifetime because it is eroded faster. However, a smaller endface can be used with less powerful electrical pulses.

Preferably, switches 24, 28 can switch in less than 50 nanoseconds (switching times less than 10 ns are preferred) Preferably, switches 24, 28 are solid state switches. Solid state switches appropriate for use in the present invention are available from Eurotek, Inc, located in Morganville, N.J.

Preferably, shunt resistor 30 R2 has a resistance much lower (e.g. an order of magnitude lower) than the resistance between inner 38 and outer 40 electrodes during an electrical discharge. In a specific embodiment where endface 60 is 25 microns across, on-state resistance (during plasma generation) between electrodes 38, 40 is about 3 kOhm and the shunt resistor R2 is about 300 Ohm.

Discharge resistor 26 and shunt resistor 30 have a resistance selected to protect the discharge switch 24 and shunt switch 28 from excessive current. The lowest resistance values of the resistors 26, 30 is set by the maximum current limit of the switches. This is a particular concern in embodiments where switches 24, 28 are solid state switches.

In operation, switches 24, 28 are operated alternately. FIG. 1 shows the discharge switch 24 in a closed or conductive state, and the shunt switch 28 in an open or nonconductive state. Switches 24, 28 are only in the state shown while a pulse is being applied to the tissue. During time periods between pulses, the shunt switch 28 is closed, and discharge switch 24 is open.

The present apparatus cuts tissue by applying short duration (i.e. less than 300 nanoseconds), high voltage pulses (i.e. greater than 1.5 kV) to the inner electrode. The pulses are created by simultaneously closing discharge switch 24 and opening shunt switch 28. Opening and closing of the switches 24, 28 is controlled by the switch controller 34. During the pulse, the discharge switch is closed, and the shunt switch is open. The pulse is actively terminated by opening discharge switch and closing shunt switch. The low resistance of the shunt resistor 30 compared to the on-state (i.e. with plasma present) resistance provides that the pulse is quickly terminated. Active termination of the pulse is greatly preferred in the present invention. Active termination of the pulse assures that the pulse is stopped abruptly before exceeding 300 ns.

FIG. 3 shows a Voltage vs. Time plot of the voltage as measured at the probe electrodes 38, 40 during a single rectangular pulse 53. The pulse 53 has a V-risetime 46 and a V-falltime 48. In the present specification, the V-risetime and V-falltime apply only to Voltage vs. Time plots. The V-risetime 46 is defined as the time required for the voltage to change from essentially 0 Volts (e.g. 100 volts) to 1.5 kV; the V-falltime 48 is defined as the time required for the voltage to change from 1.5 kV to essentially 0 Volts (e.g. 100 volts). A pulse V-duration 54 is defined as the duration the pulse exceeds 1.5 kV at the probe electrodes 38, 40.

Preferably, the voltage pulse has a somewhat rectangular shape as shown, with the voltage maintaining a plateau voltage for most of the pulse duration. This feature is provided because the capacitor 22 is large enough so that an RC time constant (C=capacitor 22 capacitance, R=resistance of circuit during discharge) is longer than the pulse duration 54. In the pulse shown, the plateau voltage is about 5 kV, the V-risetime and V-falltime are about 5 nanoseconds, and the pulse V-duration 54 is about 80 nanoseconds. The short falltime is due to the fast closing time of the shunt switch 28 and low resistance of shunt resistor R2. Falltime of the pulse is determined by discharge of the internal capacitance of the probe (about 10 pF) through R2, and by discharge of the internal capacitance of discharge switch 24 (about 20 pF) through R1+R2. R1+R2 resistance of about 600 Ohms provides a V-falltime of about 15 ns.

However, the voltage can change during the pulse duration so that a plateau voltage is not well defined. The voltage pulse can even have a peaked shape or any other shape, provided that the pulse exceeds 1.5 kV. Peaked pulse 55, for example, has approximately the same V-duration and V-risetime and V-falltime as rectangular pulse 53, and is well within the scope of the present invention.

The plateau voltage is somewhat less than the voltage provided by the high voltage supply 20. The actual plateau (or peak) voltage measured at the inner electrode depends greatly upon the impedance of the tissue during plasma formation, and the impedance of the circuit and probe. Therefore, in order to generate a desired voltage at the endface, the voltage of the high voltage source must be considerably higher than the desired endface voltage (e.g. sometimes 50–100% higher).

The voltage pulse preferably has a plateau or peak voltage between 2 kV and 15 kV. The V-risetime is less than 100 nanoseconds, preferably less than 50 nanoseconds. The V-falltime is less than 200 nanoseconds, preferably less than 100 nanoseconds, most preferably less than 50 nanoseconds. The pulse V-duration 54 is less than 300 nanoseconds. More preferably, the pulse duration is less than 150 nanoseconds, and most preferably, the pulse duration is less than 100 nanoseconds. Pulse duration can even be limited to less than 50 or 25 nanoseconds to yield exceptionally advantageous results (i.e. efficient cutting of tissue and reduced side effects from cavitation bubbles). It is noted that, for shorter pulse duration, the voltage must be higher to provide the same tissue cutting efficacy.

In a preferred embodiment, a series of pulses are applied to tissue being cut. Pulses are applied at a frequency of about 1–10000 Hz. Since the pulses are so short, this corresponds to a duty cycle much less than 0.1%. More preferably, the pulses are applied at a rate in the range of about 10–50 Hertz. It is important to note that, in the present invention, essentially zero charge (i.e. less than 1% of the charge delivered in a single pulse) passes through the probe electrodes 38, 40 between pulses. This prevents the formation of bubbles (e.g. oxygen or hydrogen bubbles) at the endface 60. This is desirable because the presence of a bubble on the endface results in plasma formation inside the bubble, instead of in the tissue 36 or liquid medium 35. Plasma formation inside the gas bubble strongly reduces pressures and expansion velocity of the overheated liquid or tissue, thereby resulting in reduced tissue cutting efficacy.

Figure 4:
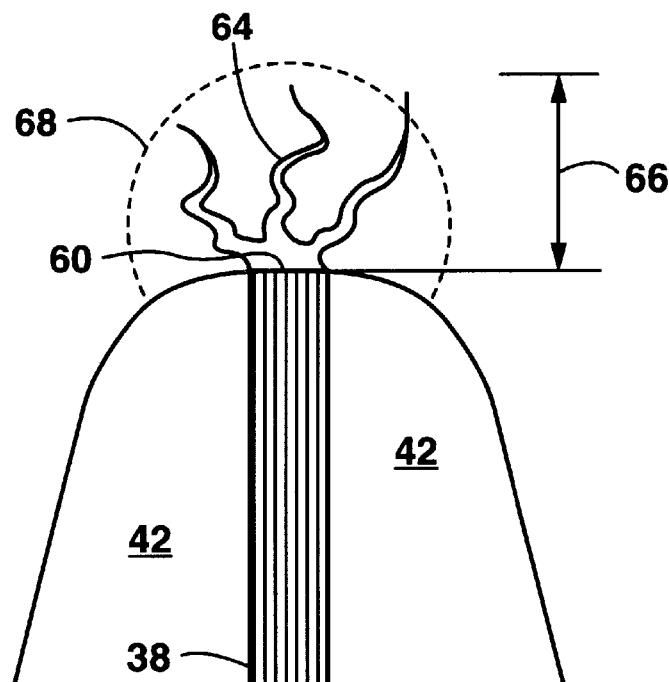
FIG. 4 shows the probe tip while an electrical pulse is applied to the probe.

FIG. 4 shows a view of the probe tip during an electrical pulse. The probe tip is surrounded by tissue 36 or liquid media 35. Plasma streamers 64 extend from the endface 60. The plasma streamers 64 extend from the endface a distance 66 which may be about 20–100 microns (a good depth range for many intraocular surgical procedures). The plasma streamers 64 can ionize, evaporate and destroy tissue in a very small region surrounding endface 60. In the present invention, cutting is provided mostly by the extremely hot plasma streamers 64. The plasma streamers 64 provide cutting action without causing excessive collateral damage to surrounding tissues.

The plasma streamers 64 are accompanied by rapidly expanding vapor and a shock wave 68 which travels in all directions away from the endface 60. The shock wave helps provide cutting action. For efficient generation of the shock wave, pulse duration should be limited to the time required for the shock wave to leave the vicinity of where energy is deposited (i.e. the vicinity of the plasma streamers). For example, for 50 micron long plasma streamers, the pulse duration should be limited to about 50 ns, assuming that the shock wave velocity is close to the speed of sound in water, 1000 m/s.

Sharp, high intensity shock waves are a particular advantage when cutting hard tissues such as lenses, lens capsules, and irises. Therefore, when cutting hard tissues, it is best to use relatively short (i.e. less than 75 nanosecond) pulses so that strong shock waves are generated.

Figure 5A:
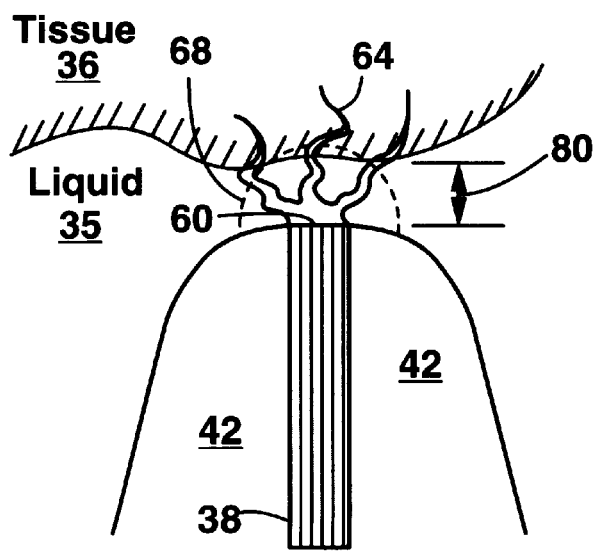
FIGS. 5A–5B show different modes of using the present invention.

FIG. 5A shows a method of the present invention in which the probe tip 37 is held away from the tissue 36 by a small distance 80 when the electrical pulse is applied to the probe. Liquid medium 35 (e.g. physiological fluid) is located between the tissue 36 and endface 60. The tissue 36 can be cut even though the endface 60 is not in direct contact with the tissue. This is because the distance 80 is small enough such that plasma streamers 64 and the shock wave 68 propagate into the tissue 36. Generally, plasma streamers can efficiently cut the tissue 36 if the distance 80 is less than about 200 microns.

Figure 5B:
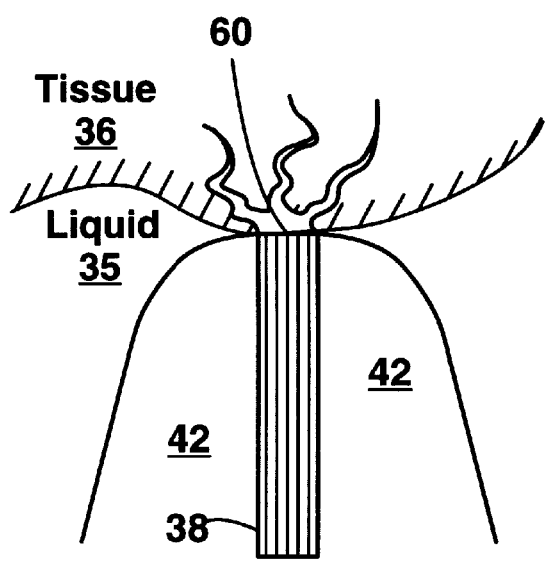

FIG. 5B shows a method where the endface 60 is in direct contact with tissue. The outer electrode 40 (not shown) is in contact with the liquid media 35, but not in contact with the tissue 36. The method of FIG. 5B generally provides deeper cutting than the method of FIG. 5A for the same pulse parameters.

The length and distribution of the plasma streamers 64 depends upon the voltage applied, pulse duration, and the surface area of the endface. The larger the surface area of the electrode, the lower will be the resistance via normal conduction (without plasma) through the liquid 35 and tissue 36. Therefore, for large endface surface area, less energy will be deposited into plasma streamer generation. However, very small endface surface area results in rapid etching of the endface and reduced probe lifetime. Therefore, an optimal endface size depends upon application (energy per pulse and required lifetime of the probe). Generally, circular endfaces having a diameter from a few microns to several tens of microns are preferred.

The length of the plasma streamers can reach about 100 microns, and further increases in plasma voltage or pulse duration results in branching of the plasma streamers (as shown in FIG. 4). The depth of the cut in tissue may exceed the length of the plasma streamers, depending on tissue properties. Generally, the softer the tissue, the deeper the cut beyond the plasma streamer length.

The rate of plasma streamer development depends on applied voltage. The plasma streamers develop faster with higher voltage. The rate of plasma streamer development is measured by the time required for the resistance between inner and outer electrodes to change from a high value (e.g. 12–15 kOhm) for ionic conduction to a low value (e.g. 2–5 kOhm) for plasma conduction. For example, with 23 pF discharge capacitor 22, and at 1.7 kV, a high to low resistance 90%–10% transition time is about 110 ns, and at 5 kV the high to low resistance 90%–10% transition time is 12 ns. Therefore, with higher applied voltages, the same size plasma streamer is generated with shorter pulses. This increases the mechanical confinement of the shock wave, thus increasing cutting efficiency.

The short V-duration (i.e. less than 200 nanoseconds) of the pulses of the present invention provides a very important benefit. The short pulse duration provides exceptionally efficient cutting of tissue for a given amount of energy applied. This is because of fast ionization due to high electric fields near the endface, as well as efficient shock wave formation. Energy-efficient cutting provides relatively high cutting power for a given cavitation bubble size (which is determined by pulse energy). Therefore the short pulses of the present invention provide effective cutting with less collateral damage to surrounding tissues. Active termination of the electrical pulses assures that the electrical pulses do not exceed a maximum desired duration.

It is also noted that cavitation bubbles can only cut very soft tissues. The method of the present invention uses plasma to provide cutting. Plasma can cut much harder and more dense tissues than cavitation bubbles, while producing less collateral damage. Plasma cutting is enhanced, and cavitation bubble effects are attenuated by using short (i.e. less than 200 nanosecond), high peak power pulses (i.e. greater than 1000 Watts).

In order to generate short, high voltage pulses, it is best to use two switches 24, 28 as shown in FIG. 1. Closing the shunt switch 28 guarantees that voltage is not applied for a duration longer than desired. The shunt switch 28 assures that the pulse duration is not defined by an excessively long exponential decay constant (e.g. hundreds of nanoseconds). The voltage at the endface, however, will be influenced by capacitance and inductance between the shunt switch and probe tip.

In some cases, impedance matching between circuit 21, probe 32 and plasma streamers 64 is a concern. For the particular device described in FIG. 1, the impedance of the tissue 36 between inner electrode 38 and outer electrode 40 is about 2–5 kOhms during plasma streamer discharge. Therefore, for impedance matching, a transmission line having a characteristic impedance of 2–5 kOhms can be connected between the probe 32 and circuit 21.

1.5 kV is generally the preferred minimum voltage for the method of the present invention because 1.5 kV is typically the minimum voltage required for ionization and plasma streamer formation in tissue using sub-microsecond pulses. 15 kV is the preferred maximum voltage because it is difficult to rapidly switch voltages greater than 15 kV; also, components capable of switching voltages greater than 15 kV are relatively costly. Voltages greater than 15 kV can be used in the present method if a fast and inexpensive switching device, flexible HV cables and proper microelectrode materials are provided. It is noted that, for high voltages, the pulse duration should be shortened. Therefore, if very high voltages are used (i.e. greater than 15 kV), then the switches must be able to produce shorter duration pulses.

In order to maintain constant per-pulse energy with rectangular (plateau) pulses, the pulse duration should scale as $1/V^2$, where V is pulse voltage. This assumes that the resistance of the discharge is the same at different voltages. However, the resistance tends to decrease with increasing voltage (as well as pulse duration), thereby requiring that the pulse duration be further shortened to preserver constant per-pulse energy.

The electrical pulses of the present invention can also be characterized in terms of power dissipated in the tissue. In some cases, describing the pulses in terms of power is a more useful characterization.

Figure 6A:
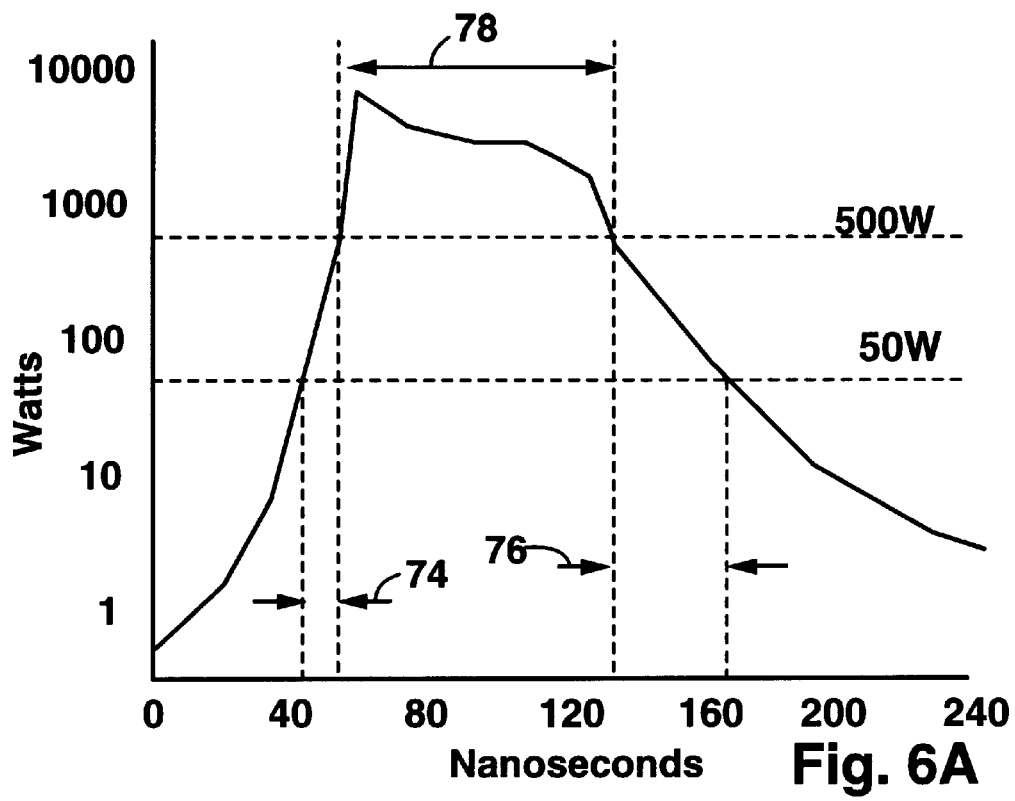
FIG. 6A shows a characterization of electrical pulses of the present invention in terms of power.

FIG. 6A shows a semilogarithmic plot of Power vs. Time for a pulse according to a preferred embodiment of the present invention. The pulse has a P-risetime 74, a P-falltime 76, and a nonzero P-duration 78 above 500 watts. In the present specification, the P-risetime, P-falltime, and P-duration apply only to Power vs. Time plots. The P-risetime is the time required for the pulse to change from 50 Watts to 500 Watts. The P-falltime is the time required for the pulse to change from 500 Watts to 50 Watts. In the present invention, the P-risetime is less than 100 nanoseconds, preferably less than 75 or 50 nanoseconds. In the present invention, the P-falltime is less than 150 nanoseconds, preferably less than 75 or 50 nanoseconds. After the pulse, the power dissipation preferably falls to 1 Watt or less, most preferably to essentially zero Watts. Preferably, the power dissipation falls from 50 Watts to less than 1 Watt within 100 nanoseconds. This prevents the formation of gas bubbles on the endface 60 between electrical pulses. In the present invention, the P-duration 78 is less than 300 nanoseconds. More preferably, the P-duration 78 is less than 200, 150, or even 75 nanoseconds. Short durations are preferred. Short duration pulses provide more effective cutting and less collateral damage to surrounding tissues. The risetimes and falltimes can also be defined in terms of changes between 800 Watts and 50 Watts.

In the present invention, 500 Watts is the minimum power dissipation because 500 Watts is approximately a lower limit for plasma streamer formation which provides reasonably effective cutting. Higher powers (e.g. 800, 1000 or 1500 Watts) provide more powerful plasma streamers which develop more quickly and provide more effective cutting. Therefore, if higher power pulses are used, then pulses can have a shorter duration and still provide equally effective cutting. The duration 78 can also be defined in terms of these high power levels.

However, the threshold for plasma streamer formation depends somewhat on the endface 60 surface area. More specifically, 500 Watts is the plasma streamer formation threshold for a circular endface of 25 microns diameter. The threshold for plasma streamer formation will be somewhat higher for larger surface area endfaces 60. The threshold for plasma streamer formation will be somewhat lower for smaller surface area endfaces 60. This is because a large endface tends to conduct current with normal, ionic conduction, thereby reducing the power available for plasma streamer formation.

Figure 6B:
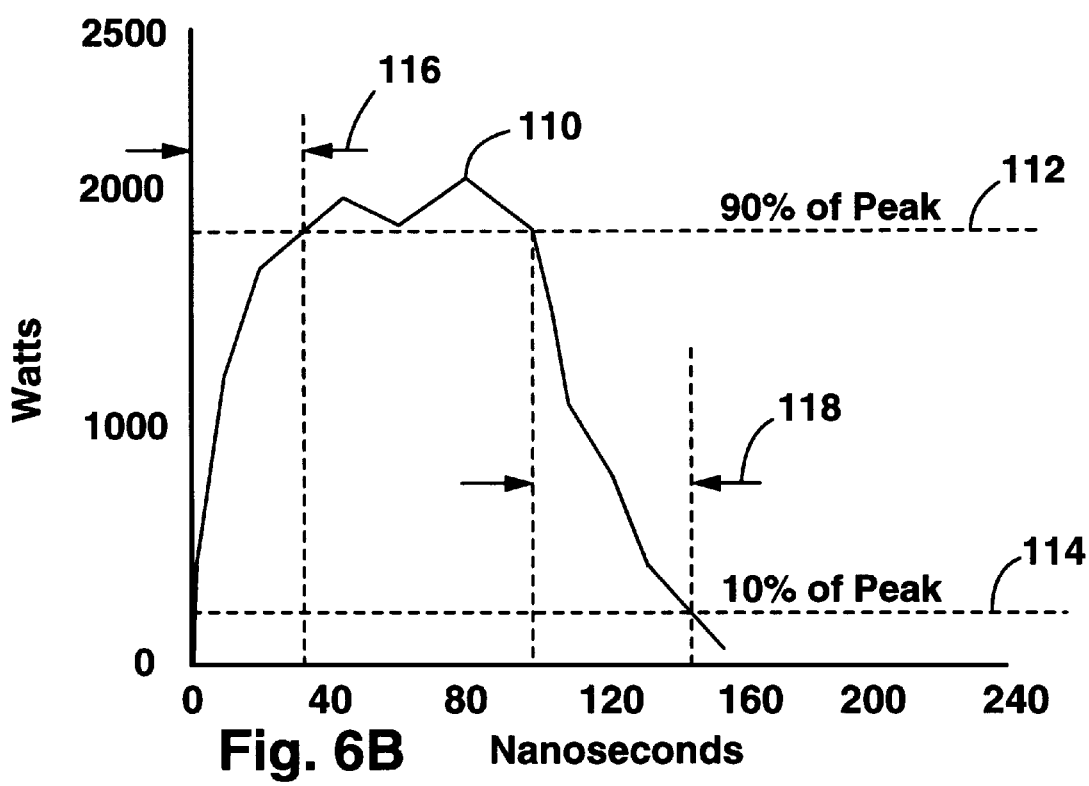
FIG. 6B shows a second characterization of electrical pulses of the present invention in terms of power.

FIG. 6B illustrates another characterization of the present method. A linear plot of pulse power versus time is shown. The pulse has a peak power dissipation 110 (in this specific example, the peak is slightly in excess of 2000 Watts). The peak 110 defines a 90%-of-peak level 112 and a 10%-of-peak level 114. In the present invention, the pulse has a 10%-to-90% risetime 116 of less than 100 nanoseconds. Preferably, the risetime is much less than 100 nanoseconds (e.g. less than 50 nanoseconds). Also in the present invention, the pulse has a 90%-to-10% falltime 118 of less than 200 nanoseconds. Also in the present invention the power dissipation is greater than 500 Watts for a duration less than 300 nanoseconds. Preferably, the duration above 500 Watts is less than 200 or 150 nanoseconds. The pulse can also have a peak greater than 800 Watts, 1000 Watts, or 1500 Watts. The peak power dissipation 110 depends upon the application. For cutting relatively soft tissues, peak 110 should be relatively low; for cutting hard tissues, peak 110 should be relatively high. For example, for cutting lenses or lens capsules, peak power may be greater than 2000 Watts.

Figure 7:
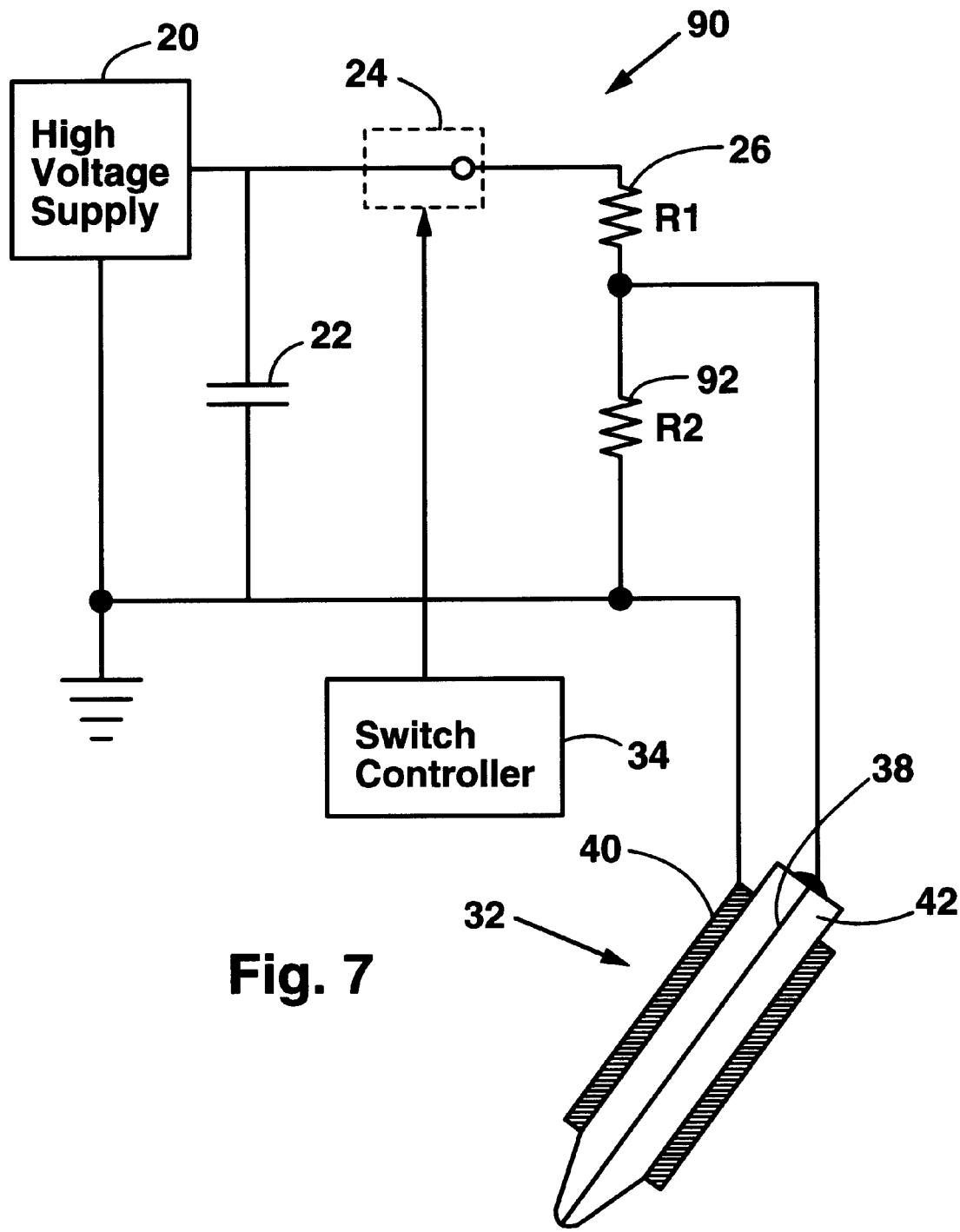
FIG. 7 shows a second embodiment of the present invention for producing electrical pulses.

FIG. 7 shows an alternative embodiment of a circuit 90 according to the present invention. The circuit 90 does not have the shunt switch 28, but only a shunt resistor 92. In this case, the shunt resistor 92 should have a resistance lower than the normal resistance (due to ionic conduction) between inner and outer electrodes (about 12–15 kOhms when a 25 micron diameter endface is used), and comparable with the resistance of the plasma streamer discharge (about 3 kOhm). For example, the shunt resistor 92 can be about 2–4 kOhms. A shunt resistor strongly reduces the power dissipation and shortens the risetime and falltime of the discharge, but does not strongly effect the plasma streamer development. This is because the shunt resistor carries relatively little current while plasma streamers exist. The pulse falltime is determined in this case by capacitor 22 and R1+R2 time constant. For pulse V- or P-duration less than 200 ns, capacitor 22 should have a capacitance less than about 70 pF. The circuit 90 produces pulses with relatively long falltimes compared to circuit 21. However, circuit 90 may be preferably for many applications because of lower cost as a result of requiring only one switch.

Figure 8:
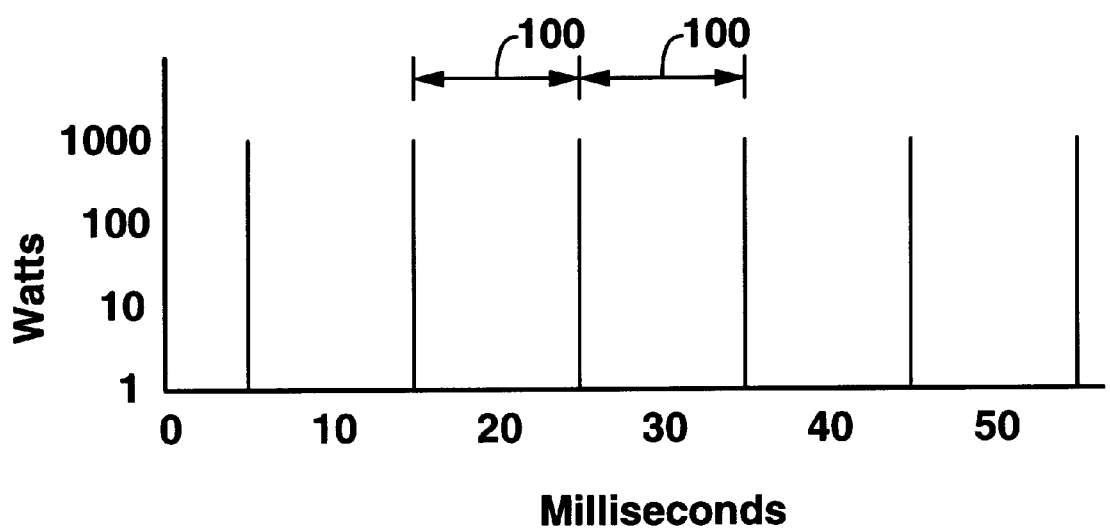
FIG. 8 shows a power versus time plot of a pulse train according to the present invention.

FIG. 8 shows a plot of power vs. time for a pulse train according to the present invention. The pulse train shown has a frequency of about 100 Hz, but can have a frequency anywhere in the range of about 1–10000 Hz. A pulse train provides essentially continuous cutting. The pulses are so short that they appear as spikes in the plot of FIG. 8. Preferably, the power dissipation in durations 100 between pulses is so low that the pulse train has an average power dissipation less than 0.2 Watts, more preferably less than 0.05 Watts or less than 0.01 Watts.

The present invention is particularly well suited for use in microsurgical procedures such as intraocular surgery. The present invention can be used in retinal surgery, cataract surgery, capsulotomy, irridotomy, as well as other intraocular surgical procedures.

The following examples are useful pulser settings for different surgical procedures. The settings are not necessarily optimized, and may be improved. In all the following examples, the endface is circular and 25 microns in diameter.

Slow Dissection of Epiretinal Membranes
 Pulse energy: 86 uJ,
 Pulse peak power: 520 W,
 Duration above 500 W: 46 ns
 50–500 Watt P-risetime: 18 ns
 500–50 Watt P-falltime: 148 ns
 Peak voltage 2.2 kV.
 Repetition rate: 10–20 Hz
Fast Dissection of Epiretinal Membranes
 Pulse energy 158 uJ,
 Pulse peak power 1150 W,
 Duration above 500 W: 138 ns
 50–500 Watt P-risetime: 7 ns
 500–50 Watt P-falltime: 118 ns
 Peak voltage 2.6 kV.
 Repetition rate: 30–50 Hz
Dissection of Lens Capsule
 Pulse energy 250 uJ,
 Pulse peak power 2100 W,
 Duration above 500 W: 160 ns
 50–500 Watt P-risetime: 6 ns
 500–50 Watt P-falltime: 110 ns
 Peak voltage 3.1 kV.
 Repetition rate: 20–40 Hz
Dissection of Lens Capsule
 Pulse energy 187 uJ,
 Pulse peak power 2200 W,
 Duration above 500 W: 124 ns
 50–500 Watt P-risetime: 4 ns
 500–50 Watt P-falltime: 80 ns
 Peak voltage 3.3 kV.
 Repetition rate: 20–40 Hz It will be clear to one skilled in the art that the above embodiment may be altered in many ways without departing from the scope of the invention. Accordingly, the scope of the invention should be determined by the following claims and their legal equivalents.

What is claimed is:

1. A method for electrosurgically cutting tissue surrounded by liquid using an electrosurgical probe, wherein the electrosurgical probe has a first electrode and a second electrode, and wherein the first electrode has an endface with area A in close proximity to the tissue, the method comprising the step of:
 a) applying to the first electrode an electrical pulse such that plasma streamers are formed from the electrode endface by an electrical discharge, wherein the electrical discharge starts in the tissue or the liquid, wherein the endface area A is less than 10000 microns$^2$, and wherein the electrical pulse has a pulse power dissipation which:
  i) is greater than 500 Watts for a nonzero duration less than 300 nanoseconds,
  ii) rises from 50 Watts to 500 Watts in less than 100 nanoseconds;
  iii) falls from 500 Watts to 50 Watts in less than 150 nanoseconds.

2. The method of claim 1 wherein pulse power is greater than 500 Watts for a duration less than 200 nanoseconds.

3. The method of claim 1 wherein pulse power is greater than 500 Watts for a duration less than 150 nanoseconds.

4. The method of claim 1 wherein pulse power is greater than 800 Watts for a duration less than 200 nanoseconds.

5. The method of claim 4 wherein pulse power falls from 800 Watts to 50 Watts in less than 150 nanoseconds.

6. The method of claim 1 wherein pulse power is greater than 1500 Watts for a duration less than 200 nanoseconds.

7. The method of claim 1 wherein pulse power rises from 50 W to 500 W in less than 50 nanoseconds.

8. The method of claim 1 wherein pulse power falls from 500 W to 50 W in less than 100 nanoseconds.

9. The method of claim 1 wherein the tissue is selected from the group consisting of lenses, lens capsules, retinal tissue, and irises.

10. The method of claim 1 wherein step (a) is repeated at a rate in the range of 10–50 Hertz.

11. The method of claim 1 wherein step (a) is repeated at a rate in the range of 1–10000 Hertz.

12. The method of claim 11 wherein between electrical pulses electrical power dissipated in the tissue is sufficiently low so that no gas bubbles are formed on the electrodes between electrical pulses.

13. The method of claim 11 wherein an average power dissipation is less than 0.2 Watts.

14. The method of claim 11 wherein an average power dissipation is less than 0.05 Watts.

15. The method of claim 1 wherein the endface area A is in the range of 200–1000 microns$^2$.

16. A method for electrosurgically cutting tissue surrounded by liquid using an electrosurgical probe, wherein the electrosurgical probe has a first electrode and a second electrode, and wherein the first electrode has an endface with area A in close proximity to the tissue, the method comprising the step of:
   a) applying to the first electrode an electrical pulse such that plasma streamers are formed from the electrode endface by an electrical discharge, wherein the electrical discharge starts in the tissue or the liquid, wherein the endface area A is less than 10000 microns$^2$, and wherein the electrical pulse has a pulse power dissipation with a peak power dissipation, wherein the pulse power dissipation:
      i) is greater than 500 Watts for a nonzero duration less than 300 nanoseconds,
      ii) rises from 10% of the peak power dissipation to 90% of the peak power dissipation in less than 100 nanoseconds;
      iii) falls from 90% of the peak power dissipation to 10% of the peak power dissipation in less than 200 nanoseconds.

17. The method of claim 16 wherein the peak power dissipation is greater than 800 Watts.

18. The method of claim 17 wherein the endface area A is in the range of 200–1000 microns$^2$.

19. The method of claim 16 wherein the peak power dissipation is greater than 1100 Watts.

20. The method of claim 16 wherein the peak power dissipation is greater than 1500 Watts.

21. The method of claim 16 wherein pulse power is greater than 500 Watts for a duration less than 200 nanoseconds.

22. The method of claim 16 wherein pulse power is greater than 500 Watts for a duration less than 150 nanoseconds.

23. The method of claim 16 wherein pulse power falls from 90% of the peak power dissipation to 10% of the peak power dissipation in less than 150 nanoseconds.

24. The method of claim 23 wherein an average power dissipation is less than 0.05 Watts.

25. The method of claim 16 wherein the tissue is selected from the group consisting of lenses, lens capsules, retinal tissue, and irises.

26. The method of claim 16 wherein step (a) is repeated at a rate in the range of 10–50 Hertz.

27. The method of claim 16 wherein step (a) is repeated at a rate in the range of 1–10000 Hertz.

28. The method of claim 27 wherein between electrical pulses electrical power dissipated in the tissue is sufficiently low so that no gas bubbles are formed on the electrodes between electrical pulses.

29. The method of claim 27 wherein an average power dissipation is less than 0.2 Watts.

30. A method for electrosurgically cutting tissue surrounded by liquid using an electrosurgical probe, wherein the electrosurgical probe has a first electrode and a second electrode, and wherein the first electrode has a endface with area A in close proximity to the tissue, the method comprising the step of:
   a) applying to the first electrode an electrical pulse such that plasma streamers are formed from the endface by an electrical discharge, wherein the electrical discharge starts in the tissue or the liquid, wherein the endface area A is less than 10000 microns$^2$, and wherein the electrical pulse has a pulse voltage which:
      i) is at least 1.5 kilovolts for a nonzero duration less than 300 nanoseconds;
      ii) rises from 100 Volts to 1.5 kV in less than 100 nanoseconds;
      iii) falls from 1.5 kV to 100 Volts in less than 300 nanoseconds.

31. The method of claim 30 wherein pulse voltage is greater than 1.5 kV for a duration less than 200 nanoseconds.

32. The method of claim 30 wherein pulse voltage is greater than 1.5 kV for a duration less than 150 nanoseconds.

33. The method of claim 30 wherein pulse voltage is greater than 2 kV for a duration less than 300 nanoseconds.

34. The method of claim 30 wherein pulse voltage is greater than 2.5 kV for a duration less than 200 nanoseconds.

35. The method of claim 30 wherein the endface area A is in the range of 200–1000 microns$^2$.

36. The method of claim 30 wherein pulse voltage rises from 100 Volts to 1.5 kV in less than 50 nanoseconds.

37. The method of claim 30 wherein pulse voltage falls from 1.5 kV to 100 Volts in less than 200 nanoseconds.

38. The method of claim 30 wherein pulse voltage falls from 1.5 kV to 100 Volts in less than 100 nanoseconds.

39. The method of claim 30 wherein the tissue is selected from the group consisting of lenses, lens capsules, retinal tissue, and irises.

40. The method of claim 30 wherein step (a) is repeated at a rate in the range of 10–50 Hertz.

41. The method of claim 30 wherein step (a) is repeated at a rate in the range of 1–10000 Hertz.

42. The method of claim 41 wherein between electrical pulses voltage between the electrodes is sufficiently low so that no gas bubbles are formed on the electrodes between electrical pulses.

43. The method of claim 41 wherein an average power dissipation is less than 0.2 Watts.

44. The method of claim 41 wherein an average power dissipation is less than 0.05 Watts.

45. An apparatus for electrosurgically cutting tissue, comprising:

a) a high voltage source for providing a voltage of at least 2 kiloVolts;

b) a probe having a first electrode for applying a high voltage pulse to the tissue, and a second electrode;

c) a discharge switch connected between the high voltage source and the first electrode so that, when closed, the discharge switch applies high voltage to the first electrode;

d) a shunt switch connected between the first electrode and the second electrode.

46. An apparatus for electrosurgically cutting tissue, comprising:

a) a high voltage source for providing a voltage of at least 2 kiloVolts;

b) a probe having a first electrode for applying a high voltage pulse to the tissue, and a second electrode;

c) a discharge switch connected between the high voltage source and the first electrode so that the discharge switch applies high voltage to the first electrode when closed;

d) a shunt resistor connected between the first electrode and the second electrode, wherein the shunt resistor has a resistance less than a normal state resistance between the first electrode and second electrode.

47. The apparatus of claim 46 wherein the shunt resistor has a resistance in the range of 1–5 kOhm.

* * * * *